(12) United States Patent
Schuind

(10) Patent No.: US 11,986,415 B2
(45) Date of Patent: May 21, 2024

(54) PRODUCTION OF A CUSTOM MEDICAL SPLINT OR BRACE FOR IMMOBILIZATION OF A SELECTED REGION OF A PATIENT'S BODY PART

(71) Applicant: Swibrace SA, Fribourg (CH)

(72) Inventor: Frédéric Schuind, Le Mont-Pélerin (CH)

(73) Assignee: Swibrace SA, Fribourg (CH)

(*) Notice: Subject to any disclaimer, the term of this patent is extended or adjusted under 35 U.S.C. 154(b) by 467 days.

(21) Appl. No.: 17/266,222

(22) PCT Filed: Aug. 6, 2019

(86) PCT No.: PCT/IB2019/056674
§ 371 (c)(1),
(2) Date: Feb. 5, 2021

(87) PCT Pub. No.: WO2020/031080
PCT Pub. Date: Feb. 13, 2020

(65) Prior Publication Data
US 2021/0298937 A1    Sep. 30, 2021

(30) Foreign Application Priority Data

Aug. 6, 2018 (EP) .................................... 18187436

(51) Int. Cl.
| | | |
|---|---|---|
| A61F 5/01 | (2006.01) | |
| A61F 5/058 | (2006.01) | |
| B29C 33/38 | (2006.01) | |
| B29C 33/40 | (2006.01) | |
| B29C 51/36 | (2006.01) | |
| B29L 31/00 | (2006.01) | |
| B33Y 80/00 | (2015.01) | |

(52) U.S. Cl.
CPC ........ *A61F 5/0118* (2013.01); *A61F 5/05866* (2013.01); *B29C 33/3842* (2013.01);
(Continued)

(58) Field of Classification Search
CPC .......................... A61F 5/0118; A61F 5/05825; A61F 5/05866; A61F 13/0293; A61F 13/04;
(Continued)

(56) References Cited

U.S. PATENT DOCUMENTS

2005/0119777 A1* 6/2005 Arbogast .............. A61F 2/5046
                                                                                700/118
2015/0328016 A1* 11/2015 Summit .................. G06F 30/00
                                                                                703/1
(Continued)

FOREIGN PATENT DOCUMENTS

DE    102012025431 A1 *  6/2014  ........... A61B 5/1077
DE    102016006113 A1 * 11/2017  ............. A41D 13/05
(Continued)

OTHER PUBLICATIONS

Translation of DE-102016006113-A1 (Year: 2017).*
(Continued)

*Primary Examiner* — Rachael E Bredefeld
*Assistant Examiner* — Seth R. Brown
(74) *Attorney, Agent, or Firm* — Taft Stettinius & Hollister LLP

(57) ABSTRACT

A method of producing a custom medical device including a splint or brace for immobilization of a selected region of a patient's body part. The custom medical device is produced in accordance with the following operations: (a) production of a three-dimensional mold of a portion of the patient's body part including the selected region onto which the desired medical device is to be placed; (b) definition of a three-dimensional shape of the desired medical device covering the selected region; (c) generation of a two-dimensional template corresponding to the defined three-dimensional shape, and which corresponds to unfolding in a two-dimensional plane of the three-dimensional shape of the
(Continued)

desired medical device; (d) production of at least one plate of moldable material in accordance with the two-dimensional template of the desired medical device; and (e) molding of the plate of moldable material onto the three-dimensional mold to shape the desired medical device.

23 Claims, 19 Drawing Sheets

(52) U.S. Cl.
CPC .............. *B29C 33/40* (2013.01); *B29C 51/36* (2013.01); *B29K 2875/00* (2013.01); *B29L 2031/753* (2013.01); *B33Y 80/00* (2014.12)

(58) Field of Classification Search
CPC ....... A61F 2/30942; A61F 2002/30952; B29C 33/3842; B29C 33/40; B29C 51/00; B29C 51/36; B29C 51/421; B29K 2875/00; B29L 2031/753; B33Y 80/00
USPC ........................................................ 602/5–7
See application file for complete search history.

(56) References Cited

U.S. PATENT DOCUMENTS

| | | | |
|---|---|---|---|
| 2015/0328840 A1* | 11/2015 | Zachariasen | G06F 30/17 700/98 |
| 2017/0079830 A1* | 3/2017 | Chhatrala | A61F 5/012 |
| 2017/0196720 A1* | 7/2017 | Hassel | A61F 5/0113 |
| 2017/0258623 A1 | 9/2017 | Lord | |

FOREIGN PATENT DOCUMENTS

| | | | |
|---|---|---|---|
| EP | 1576939 A1 | 9/2005 | |
| EP | 3050543 A1 * | 8/2016 | .............. A61F 5/01 |
| EP | 3050543 A1 | 8/2016 | |
| EP | 3315098 A1 | 5/2018 | |
| WO | 2006076932 A1 | 7/2006 | |
| WO | WO-2008086022 A1 * | 7/2008 | .............. B29C 70/30 |
| WO | 2010099130 A1 | 9/2010 | |
| WO | 2016181282 A1 | 11/2016 | |
| WO | 2016191331 A1 | 12/2016 | |
| WO | 2017024346 A1 | 2/2017 | |
| WO | 2018077912 A1 | 5/2018 | |

OTHER PUBLICATIONS

Translation of DE-102012025431-A1 (Year: 2014).*
"Polyurethane Foam Data Sheet", Oct. 2009, Cushion Source, Revision 7. (Year: 2009).*
International Search Report; European Patent Office; International Application No. PCT/IB2019/056674; dated Nov. 29, 2019; 4 pages.
Written Opinion of the International Searching Authority; European Patent Office; International Application No. PCT/IB2019/056674; dated Nov. 29, 2019; 6 pages.

* cited by examiner

PRODUCTION OF A CUSTOM MEDICAL SPLINT OR BRACE FOR IMMOBILIZATION OF A SELECTED REGION OF A PATIENT'S BODY PART

CROSS REFERENCE TO RELATED APPLICATIONS

This application is a U.S. national stage filing of International Patent Application No. PCT/IB2019/056674 filed Aug. 6, 2019, which claims priority to European Application No. 18187436.3 filed Aug. 6, 2018, the contents of each application hereby incorporated by reference in their entirety.

TECHNICAL FIELD

The present invention generally relates to the production of a custom medical splint or brace for immobilization of a selected region of a patient's body part, in particular a patient's limb.

BACKGROUND OF THE INVENTION

Methods and systems of producing custom splints or braces for immobilization of selected regions of body parts are known as such in the art.

International (PCT) Publication No. WO 2016/191331 A1 for instance discloses devices and methods for fabricating a custom splint for use in an immobilization system. One method disclosed in this publication comprises identifying a region of interest of a limb around which a splint is to be positioned, placing markers about the region of interest on the limb, and scanning the region of interest having the markers to generate data for the splint to be produced. In this particular context, photo-polymeric material is positioned around the region of interest and an image of a splint generated from the scanned data is projected onto the photo-polymeric material, after which the image area of the photo-polymeric material is cured and remaining uncured portions of the photo-polymeric material are removed to provide the splint.

International (PCT) Publication No. WO 2016/181282 A1 discloses a method for making an orthosis of a body part of a person, the method comprising (i) measuring the body part with a shape and in a pose in order to obtain measurement data of the body part, (ii) correlating the measurement data of the body part to a predetermined statistical shape model of a corresponding reference body part in order to calculate parameters of the statistical shape model, (iii) digitally forming an orthosis model on the basis of the statistical shape model with the known parameters, and (iv) producing the orthosis via a CAD/CAM system on the basis of the digitally formed orthosis model. In this context, it is in particular contemplated to produce the orthosis by means of a 3D printer. Direct moulding of a splint or brace onto the relevant portion of the patient's body part is also known as such in the art and widely applied in practice using e.g. mineral plaster casting materials, thermoformable materials or resin impregnated fabric materials. Situations may however occur where direct moulding of the splint or brace is not possible, for instance in case of a fracture or in case of the presence of cutaneous lesions or wounds in the region to be immobilized. This approach is likewise not convenient in cases where the patient cannot stand still during moulding of the splint or brace, due e.g. to a neurologic pathology such as Parkinson's disease, or in the event that the patient is simply not physically available for carrying out direct moulding of the splint or brace.

These known solutions have certain limitations and drawbacks, especially in terms of manufacturing costs, robustness of the resulting custom splints or braces and compliance thereof with medical requirements.

There is therefore a need for an improved solution.

SUMMARY OF THE INVENTION

A general aim of the invention is to provide an improved solution for the production of a custom splint or brace for immobilization of a selected region of a patient's body part.

This general aim is achieved thanks to the solution defined in claim 1.

Advantageous embodiments of the invention form the subject-matter of the dependent claims and are discussed below.

BRIEF DESCRIPTION OF THE DRAWINGS

Other features and advantages of the present invention will appear more clearly from reading the following detailed description of embodiments of the invention which are presented solely by way of non-restrictive examples and illustrated by the attached drawings in which:

FIGS. 3A and 36 are photographic illustrations of a three-dimensional mould produced on the basis of the three-dimensional digital model of FIGS. 2A to 2C;

DETAILED DESCRIPTION OF EMBODIMENTS OF THE INVENTION

Figure 1A:
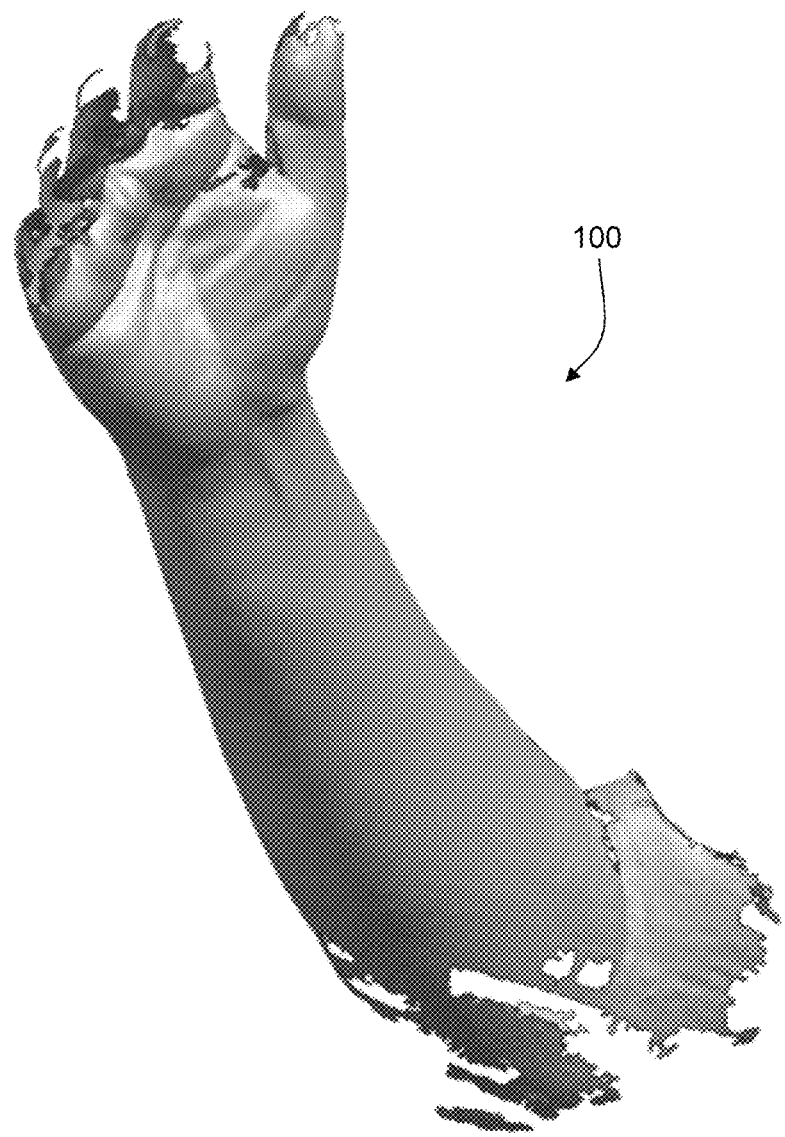
FIGS. 1A and 1B are illustrations of a three-dimensional scan of a portion of a patient's body part, namely of a human's right forearm, which three-dimensional scan was obtained by three-dimensional imaging of the patient's body part.

The present invention will be described in relation to various illustrative embodiments. It shall be understood that the scope of the invention encompasses all combinations and sub-combinations of the features of the invention disclosed herein.

The expression "patient" used herein should be understood as encompassing any human or animal patient. The present invention is therefore applicable to any therapeutic treatment necessitating immobilization of a selected region of a body part of a human or animal.

The invention will be described in the particular context of the production of a custom splint or brace used for immobilization of a human's wrist. An example of such a custom splint or brace, designated by reference numeral 500, is shown in the photographic illustrations of FIGS. 7A and 7B. The custom splint or brace 500 is shown here placed on a selected region A (i.e. the wrist) of the relevant patient's limb L (i.e. the right forearm). It should be appreciated however that the invention is applicable to the production of splints or braces for immobilization of any selected region of a patient's body part, be it the upper or lower limbs or any other body part to be immobilized by means of a splint or brace, such as the patient's face or torso for instance. It should further be appreciated that the invention may also be applicable to the production of custom-made braces or exoskeleton elements, such as immobilization devices for radiotherapy, protective braces for sports, games and like applications, or for veterinary immobilization. In other words, the medical splint or brace of the invention may be configured to act as an external immobilization device placed around the selected region of the patient's body part.

The invention can also be applied to the production, pre-operatively or in the operation room, of custom-made implants based on pre- or peroperative imaging. Such custom-made implants may especially be made of cement or implantable thermoplastic materials. One illustrative example is the manufacture of a custom-made cement spacer (usually loaded with antibiotics) intended to replace a bone flap after craniectomy, particularly indicated in the case of an infection and/or in case of poor prognosis of survival. In other words, the medical splint or brace of the invention may also be configured to act as an implantable immobilization device placed in the selected region of the patient's body part.

According to the invention, the custom medical splint or brace is produced in accordance with the following sequences of operations, namely:

(a) production of a three-dimensional mould of a portion of the patient's body part comprising the selected region of the patient's body part onto which the desired medical splint or brace is to be placed;

(b) definition of a three-dimensional shape of the desired medical splint or brace covering the selected region of the patient's body part onto which the desired medical splint or brace is to be placed;

(c) generation of a two-dimensional template of the desired medical splint or brace corresponding to the defined three-dimensional shape, which two-dimensional template corresponds to unfolding in a two-dimensional plane of the three-dimensional shape of the desired medical splint or brace;

(d) production of at least one plate of mouldable material in accordance with the two-dimensional template of the desired medical splint or brace; and (e) moulding of the plate of mouldable material onto the three-dimensional mould to shape the desired medical splint or brace.

In other words, according to the invention, moulding of the plate of mouldable material is carried out on the three-dimensional mould of the relevant portion of the patient's body part, rather than on the patient's body part directly. This ensures production of a high-quality splint or brace that best matches the patient's morphology, without this requiring immobilization of the patient during the entire moulding phase. As a matter of fact, the actual presence of the patient during the moulding phase is not required at all.

The production of the necessary three-dimensional mould may be carried out in different ways. One solution may simply consist in producing the three-dimensional mould by direct moulding of the patient's body part. By way of preference, the three-dimensional mould is produced on the basis of a three-dimensional digital model of the relevant portion of the patient's body part as discussed with reference to FIGS. 1A-1B, 2A-2C and 3A-3B.

Figure 1B:
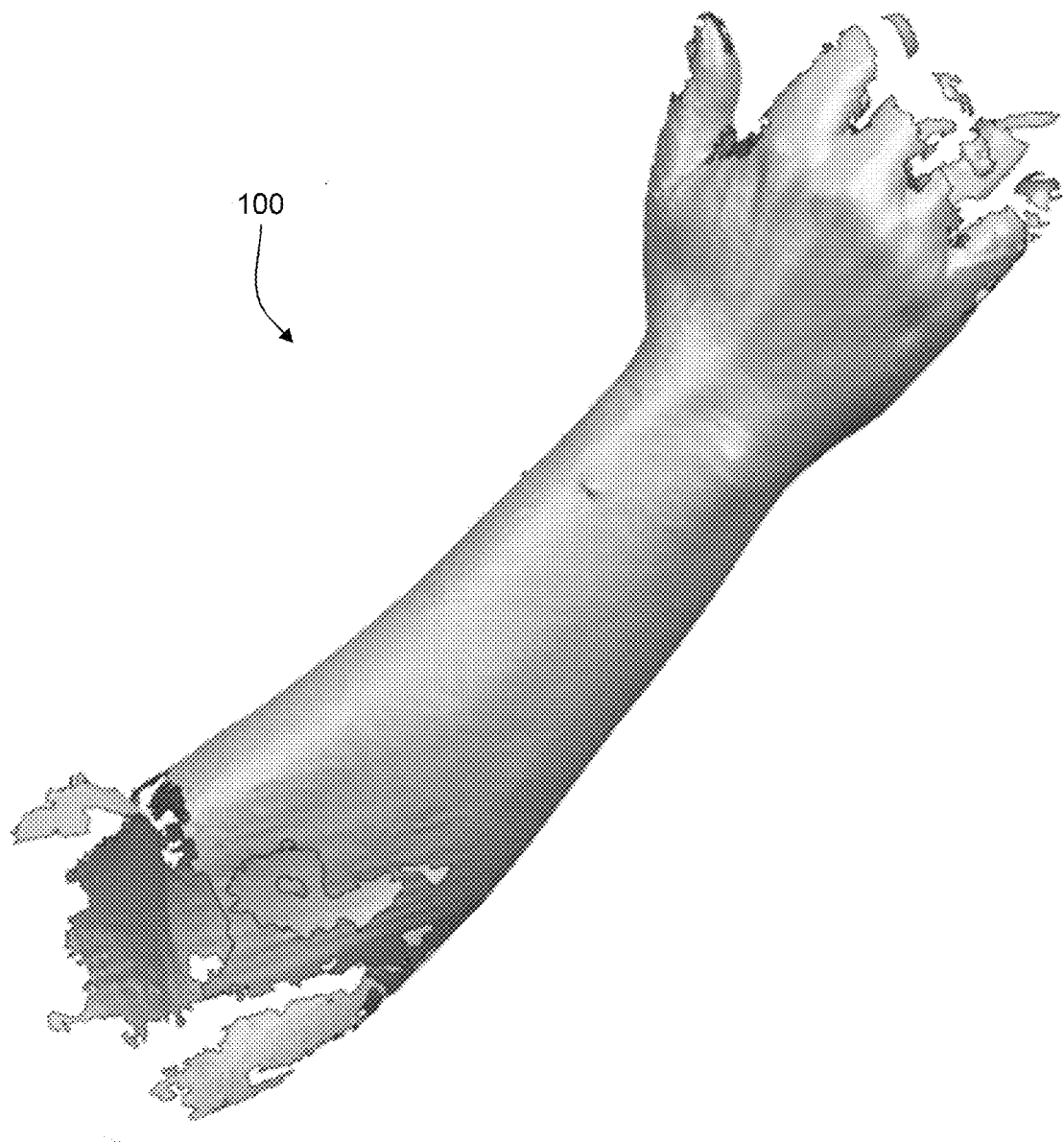

FIGS. 1A and 1B are illustrations of a three-dimensional scan 100 of a portion of the patient's limb L, which three-dimensional scan 100 was obtained by three-dimensional imaging of the relevant portion of the patient's limb L. Three-dimensional imaging systems suitable for scanning and acquiring the three-dimensional scan 100 are known as such in the art. The three-dimensional scan 100 can be obtained by direct imaging of the relevant portion of the patient's body part onto which the custom splint or brace is to be placed. In the event that the custom splint or brace is intended for the immobilization of a selected region of a patient's limb, it is also possible to generate a relevant three-dimensional scan by imaging the patient's contralateral limb and mirroring the imaged data, as taught for instance in European Patent Publication No. EP 3 315 098 A1 and International (PCT) Publication No. WO 2018/077912 A1, the content of which is incorporated herein by reference in its entirety.

Figure 2A:
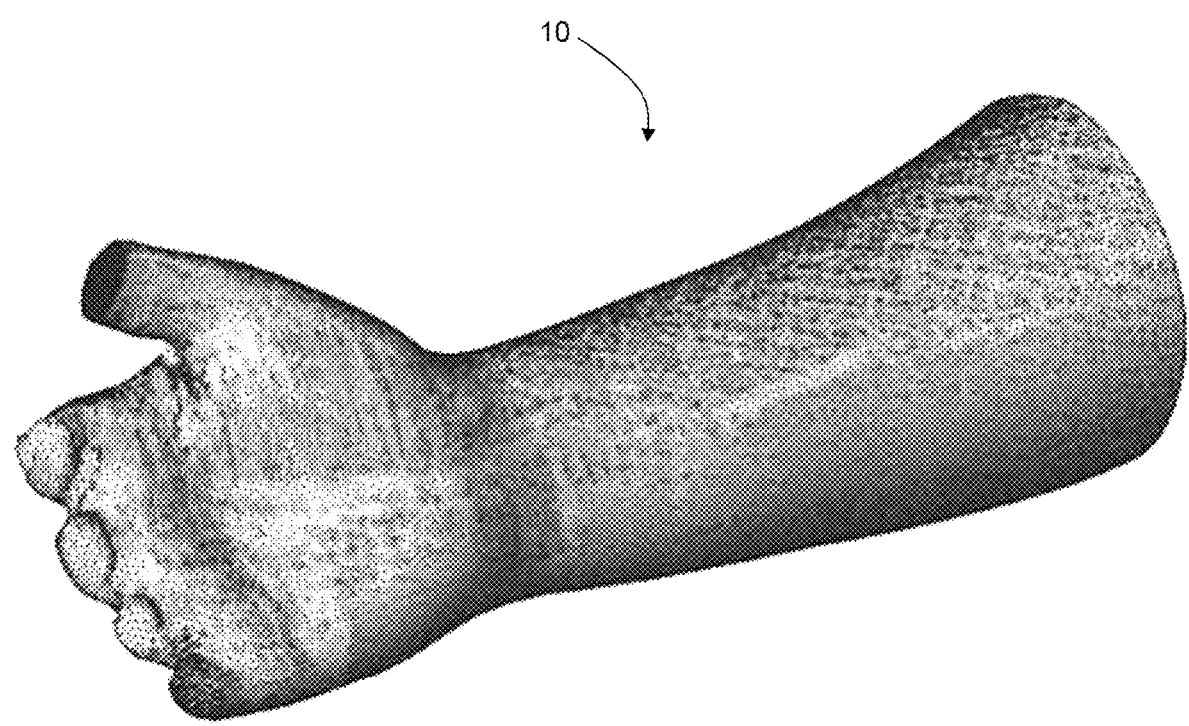
FIGS. 2A to 2C are views taken under different viewing angles of a three-dimensional digital model generated on the basis of the three-dimensional scan of FIGS. 1A and 1B.
Figure 2B:
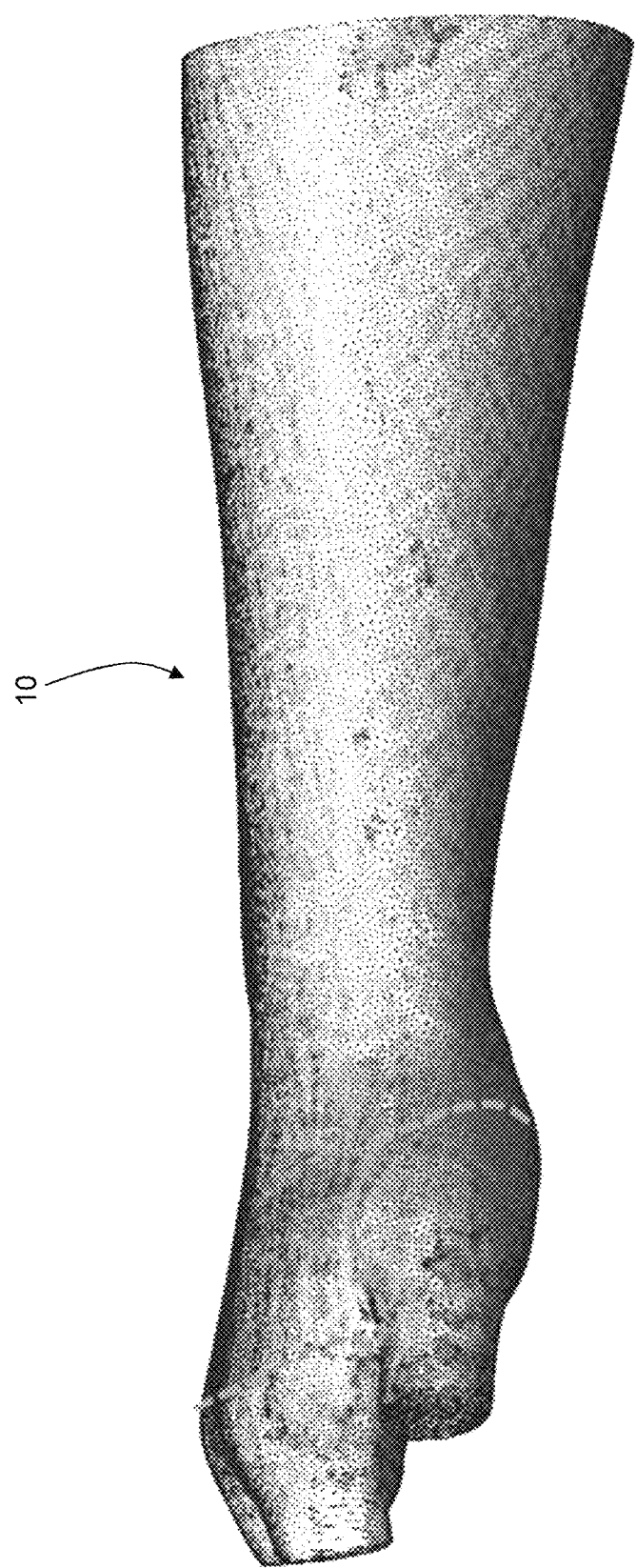
Figure 2C:
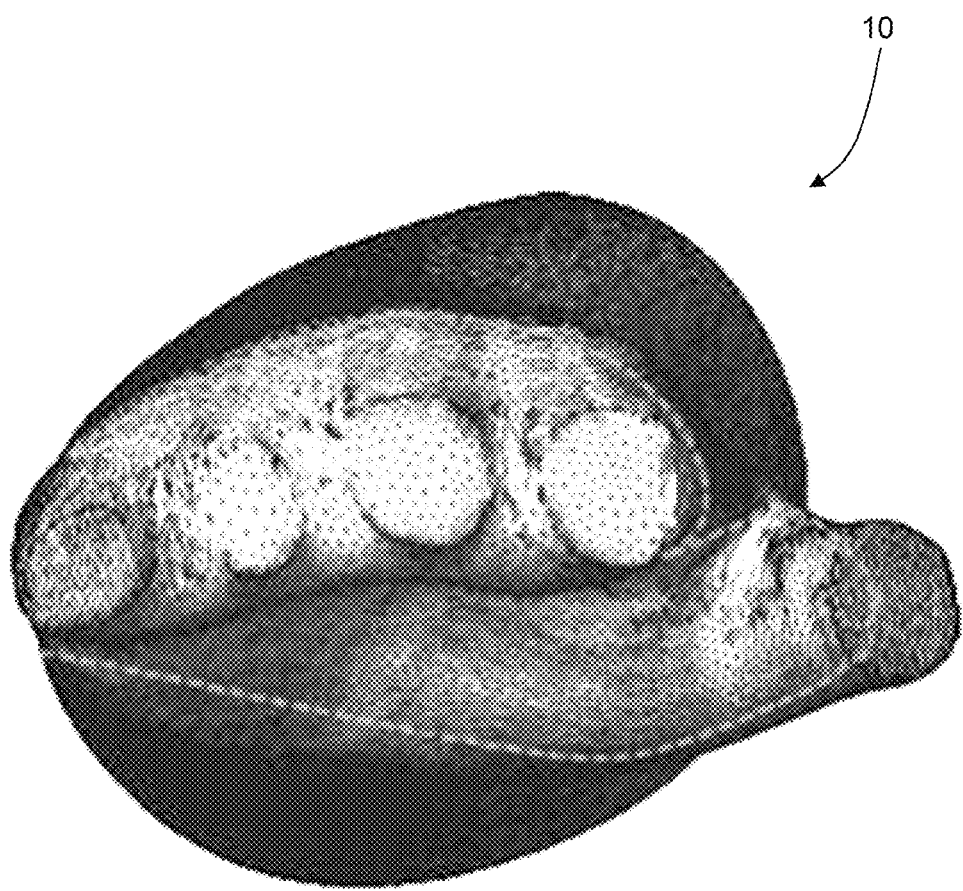

A three-dimensional digital model 10 of the relevant portion of the patient's limb L, as illustrated in FIGS. 2A-2C can then be produced on the basis of the aforementioned three-dimensional scan 100. This could suitably be carried out on a CAD system adapted to process the three-dimensional data of the relevant three-dimensional scan 100, cleaning and removing undesired data that may have been acquired as part of the three-dimensional imaging process. The three-dimensional model 10 is defined with due consideration of the selected region A of the patient's body part L onto which the desired splint or brace is to be placed. In other words, unnecessary data, outside of the selected region A of the patient's body part L can be omitted in the three-dimensional model 10.

Once the three-dimensional model 10 has been defined, a three-dimensional mould of the relevant portion of the patient's body part L can be produced, for instance by milling on a CNC machine. Additive manufacturing processes (such as 3D printing) could also be contemplated in order to produce the required three-dimensional mould.

Figure 3A:
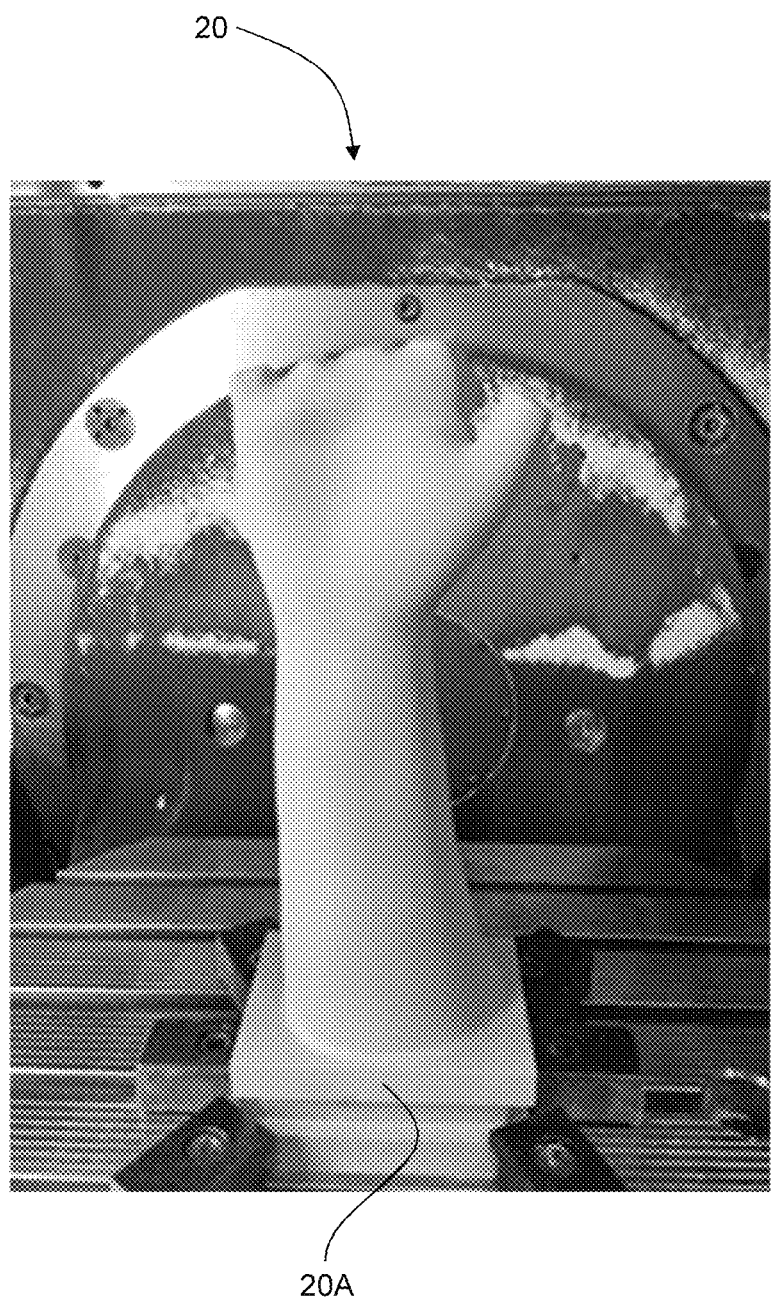
Figure 3B:
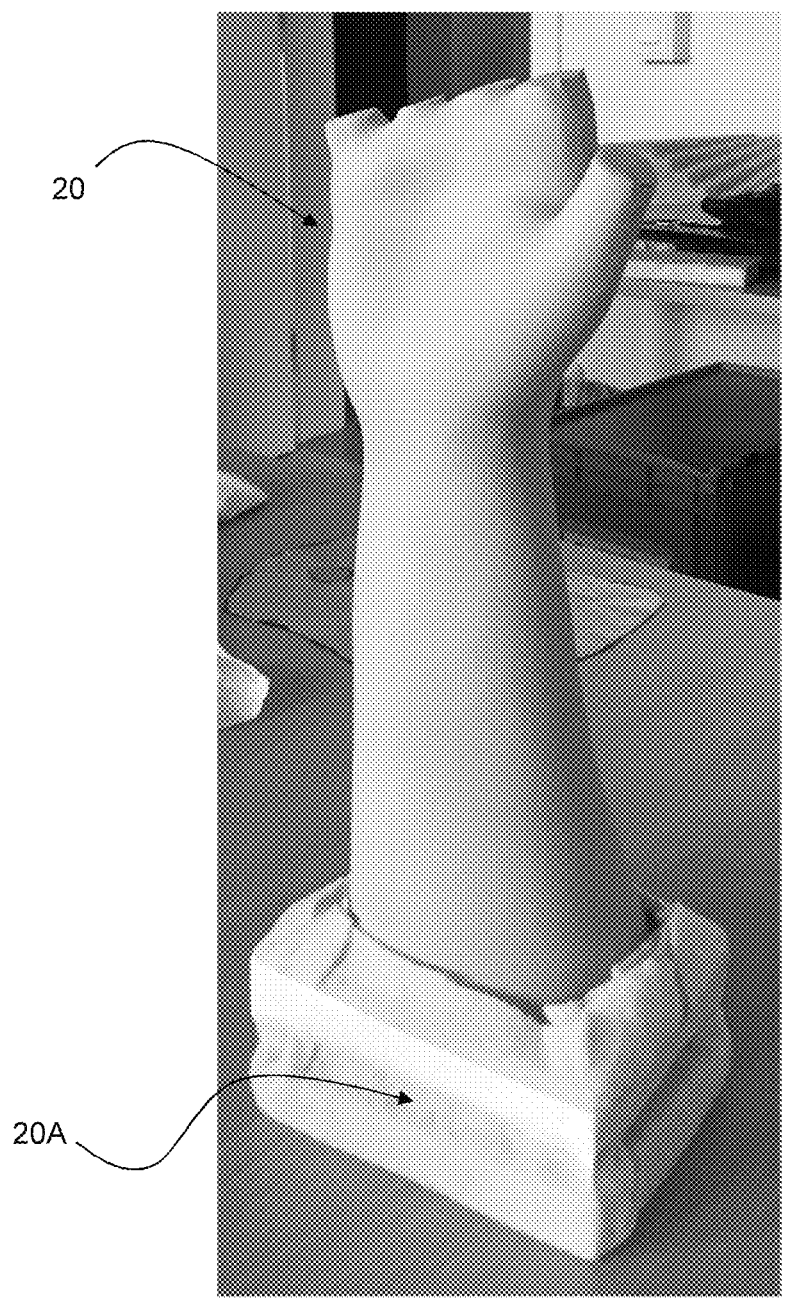

In accordance with a preferred embodiment of the invention, the three-dimensional mould is produced by milling of a raw block of material, for instance a block of polyurethane. FIGS. 3A and 3B show a three-dimensional mould 20 of the relevant portion of the patient's limb L as milled on a CNC milling machine using the three-dimensional digital model 10 of FIGS. 2A-2C. FIGS. 3A and 3B further show that the three-dimensional mould 20 is advantageously provided with a base member 20A designed to support the three-dimensional mould 20 in a substantially vertical configuration. This may facilitate the subsequent moulding phase of the custom splint or brace per se.

Figure 8A:
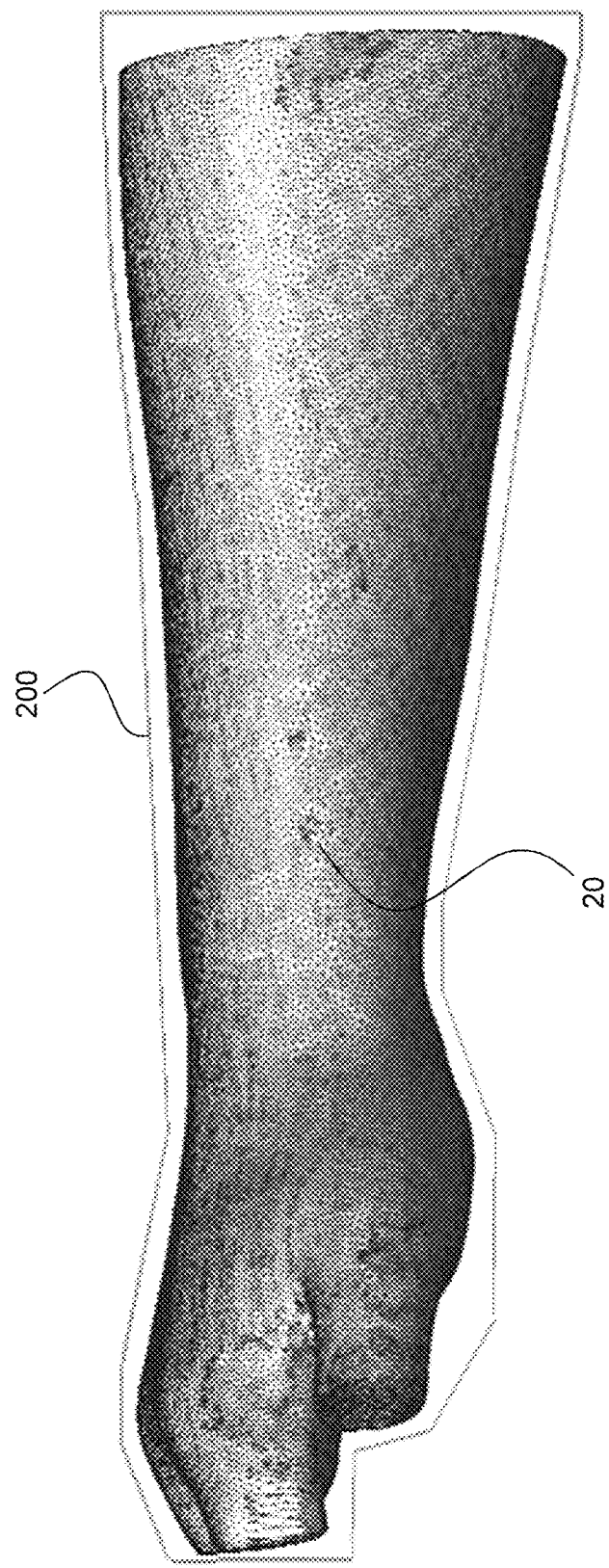
FIGS. 8A and 8B are schematic illustrations of standardized pre-processed blocks of material matching a given population of patients, which standardized pre-processed block can be subjected to milling or additive manufacturing to produce the required three-dimensional mould.
Figure 8B:
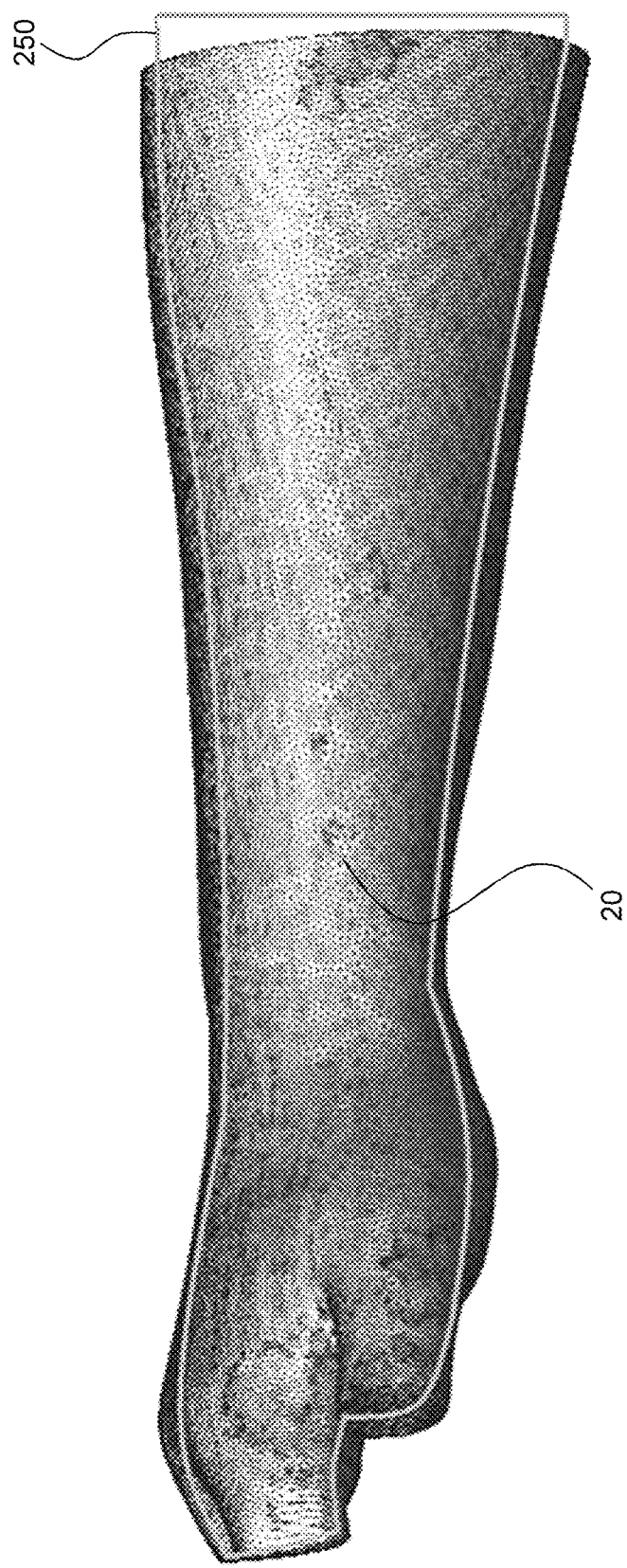

In order to reduce lead times, the three-dimensional mould 20 could be produced from a standardized pre-processed block of material 200, as schematically depicted in FIG. 8A, larger in size than the desired three-dimensional mould 20 and matching a given population of patients, which standardized pre-processed block 200 is subjected to milling. In other words, the relevant standardized pre-processed block of material 200 that best matches the general morphology of the patient would be selected first and then subjected to a final milling operation to remove the necessary material, substantially reducing the amount of material to be removed during the milling operation and thus reducing the amount of time necessary to produce the three-dimensional mould 20. With this approach, the relevant three-dimensional mould 20 may be produced in a very short timeframe of the order of 15 to 30 min, depending on the mould complexity.

By way of alternative, the three-dimensional mould 20 could be produced from a standardized pre-processed block of material 250, as schematically depicted in FIG. 81, smaller in size than the desired three-dimensional mould 20 but likewise matching a given population of patients, which standardized pre-processed block 250 is subjected to additive manufacturing. In other words, the relevant standardized pre-processed block of material 250 that best matches the general morphology of the patient would be selected first and then subjected to additive manufacturing (such as 3D printing), likewise reducing the amount of time necessary to produce the three-dimensional mould 20.

Definition of the three-dimensional shape of the desired medical splint or brace covering the selected region A of the patient's body part L onto which the desired medical splint or brace is to be placed can also be carried in different ways. One particularly advantageous solution may consist in defining the three-dimensional shape of the desired medical splint or brace in a digital environment (e.g. a suitable CAD system) by delimiting the three-dimensional shape of the desired splint or brace onto the aforementioned three-dimensional digital model 10. In such case, a two-dimensional template could directly be generated by digitally processing the three-dimensional shape to unfold the three-dimensional shape in a two-dimensional plane. The computer-generated two-dimensional template could then be used to produce a physical template or directly the plate of mouldable material per se. This computer-based approach is particularly advantageous in that the computer-generated two-dimensional template can further be processed in order to incorporate patient-specific features or other desired features, such as custom apertures and/or cut-outs.

Figure 4:
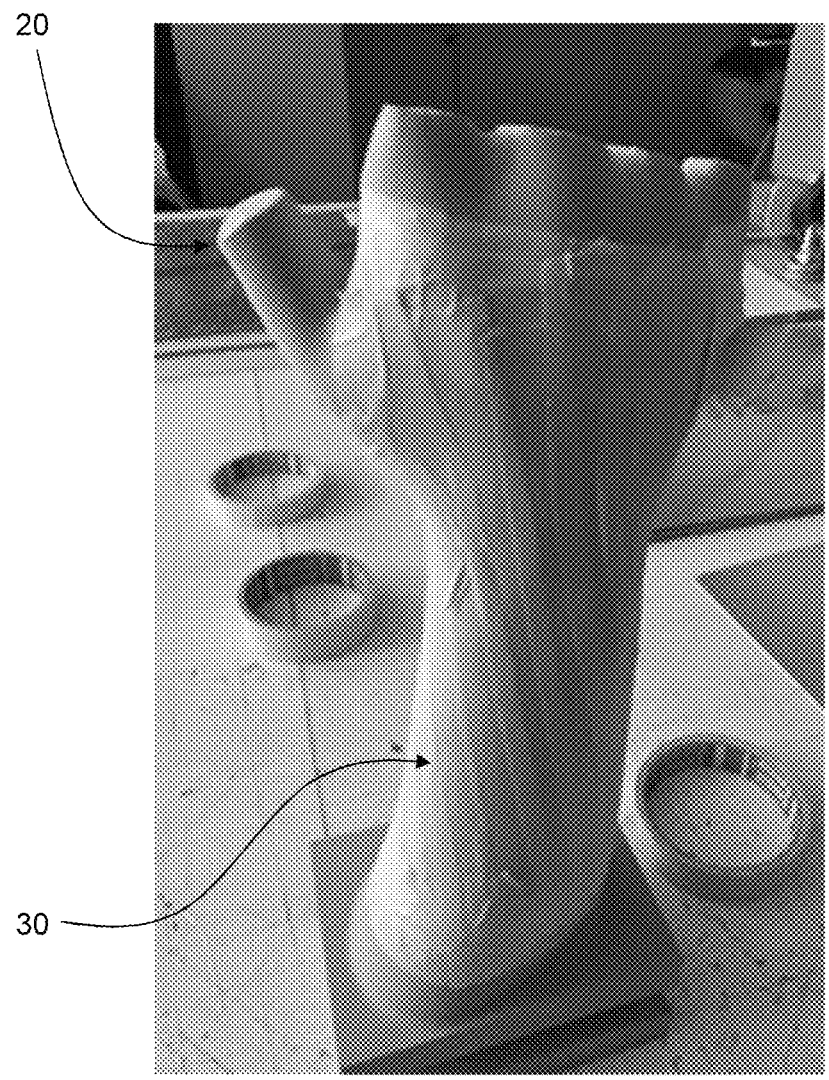
FIG. 4 is a photographic illustration of the three-dimensional mould of FIGS. 3A and 3B onto which support material has been applied, here in the form of tape material, with a view to define a three-dimensional shape of a desired splint or brace to be placed and delimiting a selected region of the patient's limb, namely the region of the wrist, onto which the desired medical splint or brace is to be placed.

A more direct approach may simply consist in using the aforementioned three-dimensional mould 20 to generate the required two-dimensional template as discussed with references to FIGS. 4 and 5A-5D. FIG. 4 is a photographic illustration of the three-dimensional mould 20 of FIGS. 3A and 3B onto which support material, designated by reference numeral 30, has been applied with a view to define the three-dimensional shape of the desired splint or brace. This is achieved by covering the selected region where the desired medical splint or brace is to be placed and delimiting the three-dimensional shape of the desired medical splint or brace by means of the support material 30. The support material 30 may for instance be tape material applied by hand onto the three-dimensional mould 20 to form and shape the desired three-dimensional shape of the splint or brace.

Once the desired three-dimensional shape of the splint or brace has been formed onto the three-dimensional mould 20, the support material 30 is removed from the three-dimensional mould 20 and flattened on a suitable planar surface to cause unfolding of the three-dimensional shape in a two-dimensional plane. Due to the relatively complex shape, complete flattening of the support material may not be possible, but this is not critical since imperfections will be compensated during moulding of the mouldable plate onto the three-dimensional mould.

Figure 5A:
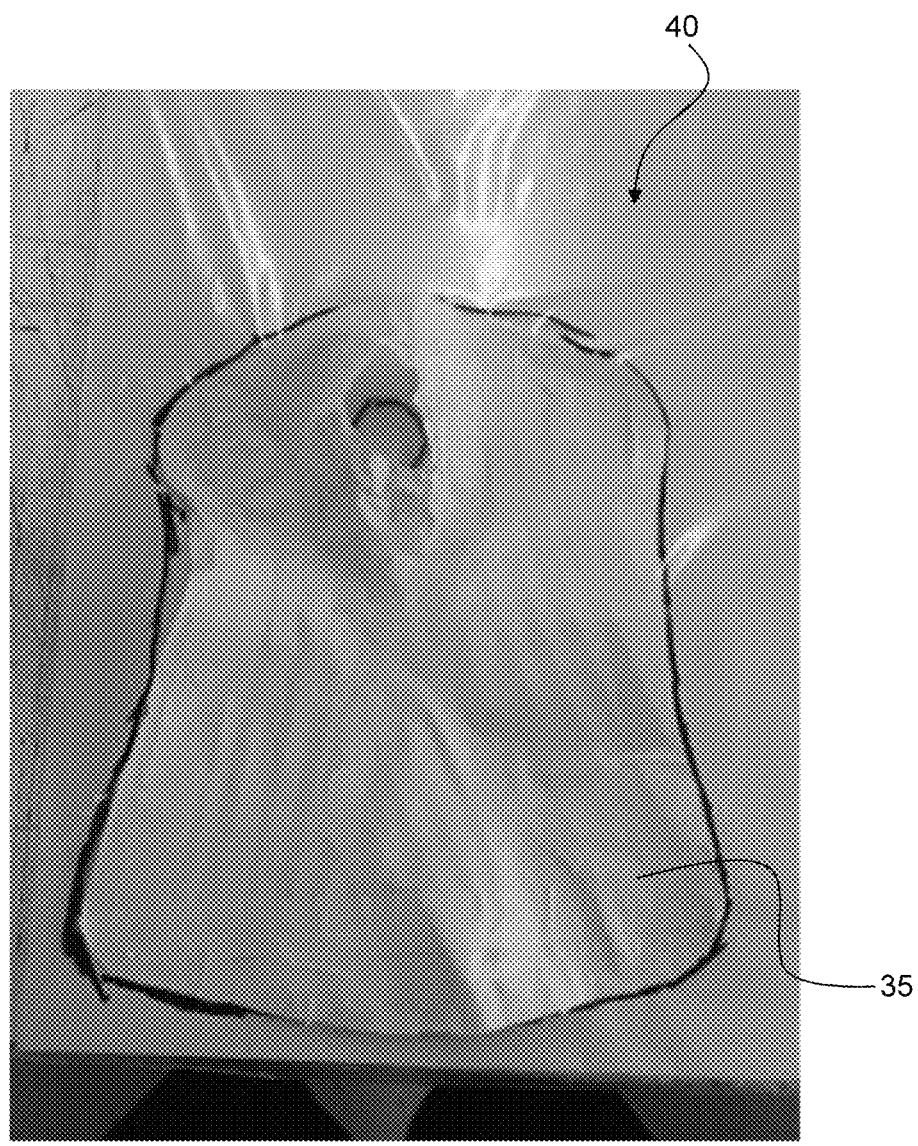
FIGS. 5A and SB are photographic illustrations of the support material, with the delimited three-dimensional shape of the desired splint or brace, after removal from the three-dimensional mould and flattening of the support material to cause unfolding of the three-dimensional shape in a two-dimensional plane.

FIG. 5A shows flattening of the support material, designated here by reference numeral 35 for the sake of distinction, onto a sheet of template material 40, such as transparent material. The support material 35 is used to replicate the outline thereof onto the sheet of template material 40 and cut a corresponding two-dimensional template 45 therein (see FIGS. 5B and 5C).

Figure 5B:
FIG. 5C is a photographic illustration of a two-dimensional template of the desired medical splint or brace corresponding to unfolding of the three-dimensional shape in the two-dimensional plane.
FIG. 5D is a photographic illustration of a plate of mouldable material, such as Orfit™ material, produced in accordance with the two-dimensional template of FIG. 5C.
Figure 5C:
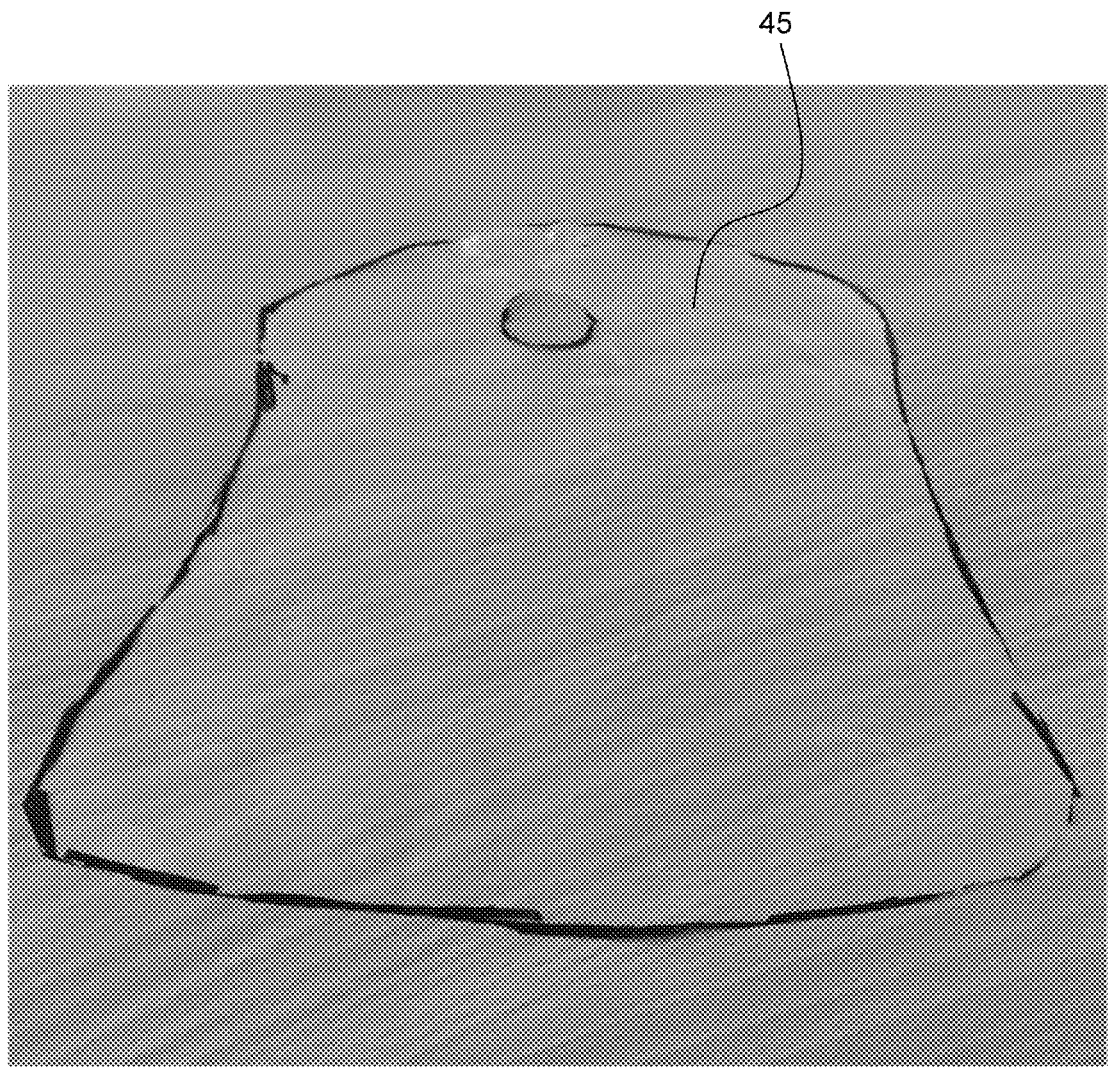
Figure 5D:
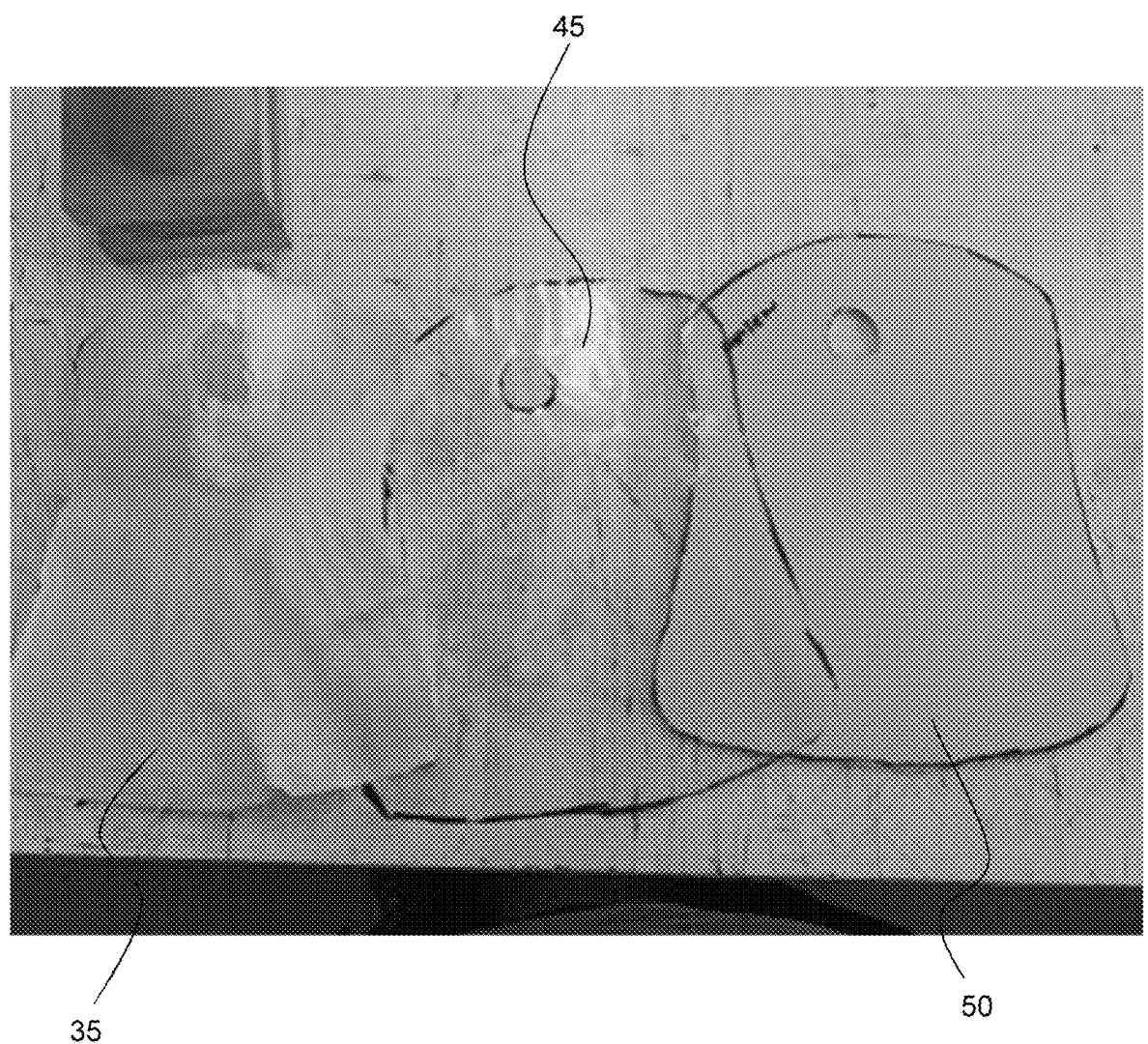

The aforementioned two-dimensional template (be it a physical template 45 as shown in FIGS. 5B and 5B or a computer-generated template as discussed above) is then used to produce at least one plate of mouldable material 50 as depicted e.g. in FIG. 5D. In the context of the presently-described embodiment, a single plate of mouldable material 50 is advantageously used, but multiple plates of mouldable material could be used to produce a given splint or brace.

The plate of mouldable material 50 is preferably made of a thermoformable material, which is heated to an activation temperature to allow moulding thereof onto the three-dimensional mould 20. A suitable material may be Orfit™ material as manufactured by company Orfit Industries (www.orfit.com). Successful tests have been carried out by the Applicant using the Orfibrace™ product, which is a thermoformable material having an activation temperature of the order of 60° to 80°. In that respect, the three-dimensional mould 20 is preferably made of a material (such as polyurethane) having a melting point that exceeds the activation temperature of the thermoformable material, thereby ensuring that the plate of thermoformable material can suitably be moulded onto the three-dimensional mould 20 without causing deformation of the three-dimensional mould 20.

Polyurethane is a particularly adequate material for production of the three-dimensional mould 20 especially due to its ease of machining, structural strength and stability, resistance to deformation, and low coefficient of thermal expansion. Polyurethane material is furthermore readily available on the market and at a relatively low cost. In addition, polyurethane waste is non-toxic and potentially recyclable. Exemplary polyurethane products include polyurethane machinable board material sold by company RAMPF (www.ramof-arouo.com) under product references RAKU-TOOLS MB-0670 and SB-0470, which machinable board material is available in various dimensions.

Thermoformable materials (like Orfit™ materials) are used by way of preference in the context of the present invention due to their ease of use, excellent drapability, and good resistance and robustness. Thermoformable materials like Orfit™ materials furthermore already have a well-established medical use, are available in perforated form, have antibacterial properties, and can be adjusted or reshaped if necessary by local application of heat.

Figure 6A:
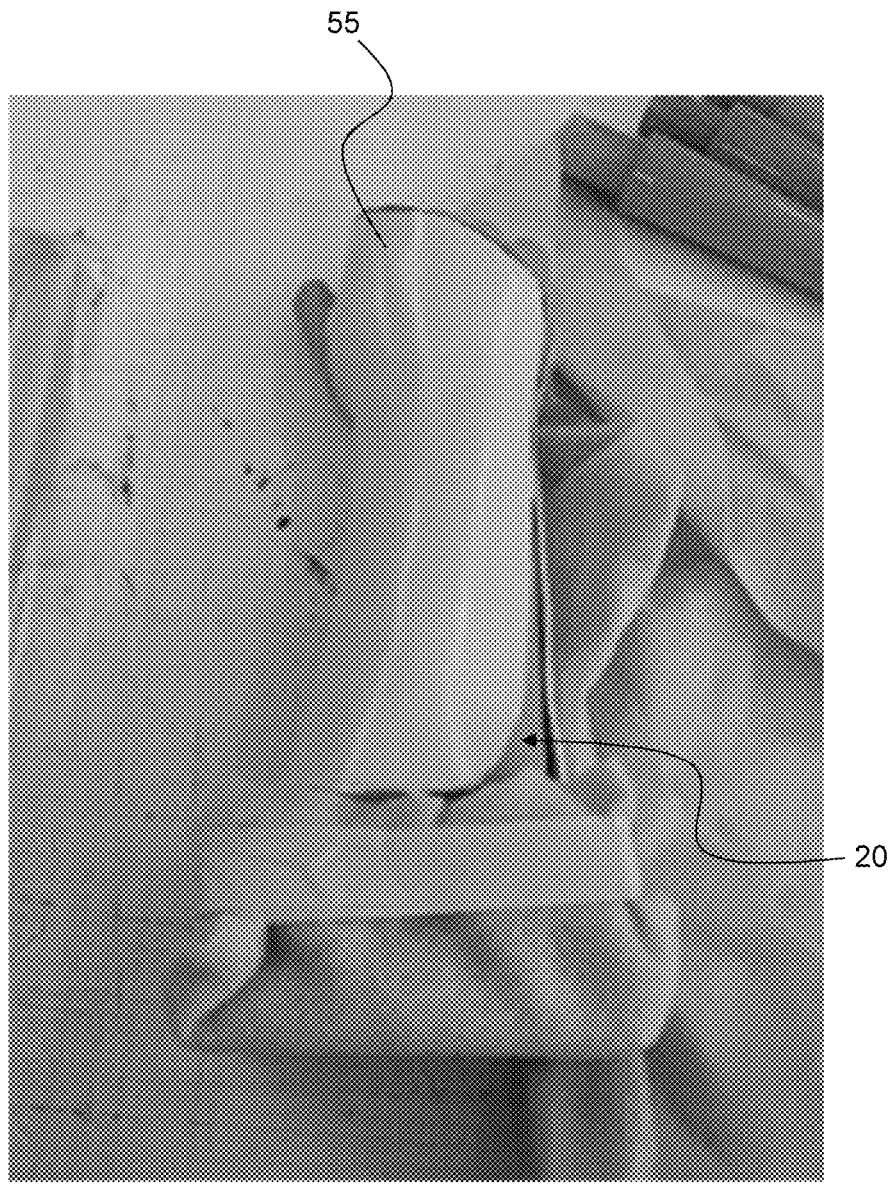
FIG. 6A is a photographic illustration of the plate of mouldable material of FIG. 5D as roughly moulded onto the three-dimensional mould of FIGS. 3A and 38.

The plate of mouldable material 50, once heated to the required activation temperature, can be moulded onto the three-dimensional mould 20 entirely by hand. By way of alternative, moulding of the plate of mouldable material 50 onto the three-dimensional mould 20 can be carried out under vacuum as described with reference to FIGS. 6A-6C. In that context, after having roughly moulded the plate of mouldable material onto the three-dimensional mould 20 (see FIG. 6A, where the roughly moulded plate is designated by reference numeral 55), the three-dimensional mould 20 can be placed, together with the roughly moulded plate 55, into a vacuum bag 60 as shown in FIG. 68. Application of vacuum to the vacuum bag, as shown in FIG. 6C (where the relevant vacuum bag is designated by reference numeral 60*) causes final moulding of the plate of mouldable material onto the three-dimensional mould 20, the finally moulded plate of mouldable material being designated in this final state by reference numeral 55*.

Figure 6B:
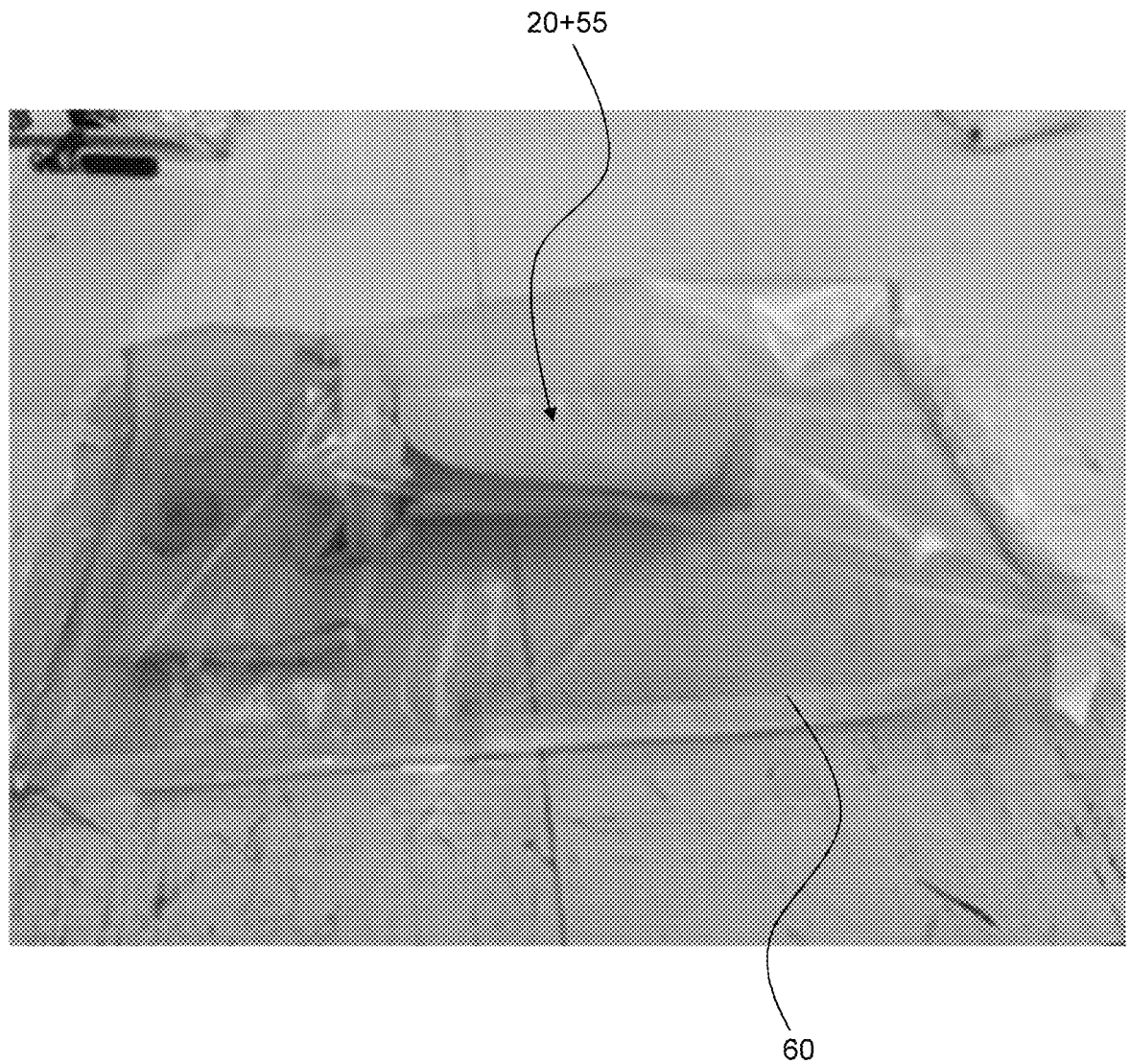
FIG. 6B is a photographic illustration of a vacuum bag containing the three-dimensional mould and roughly moulded plate of mouldable material of FIG. 6A in a state prior to application of vacuum.
Figure 6C:
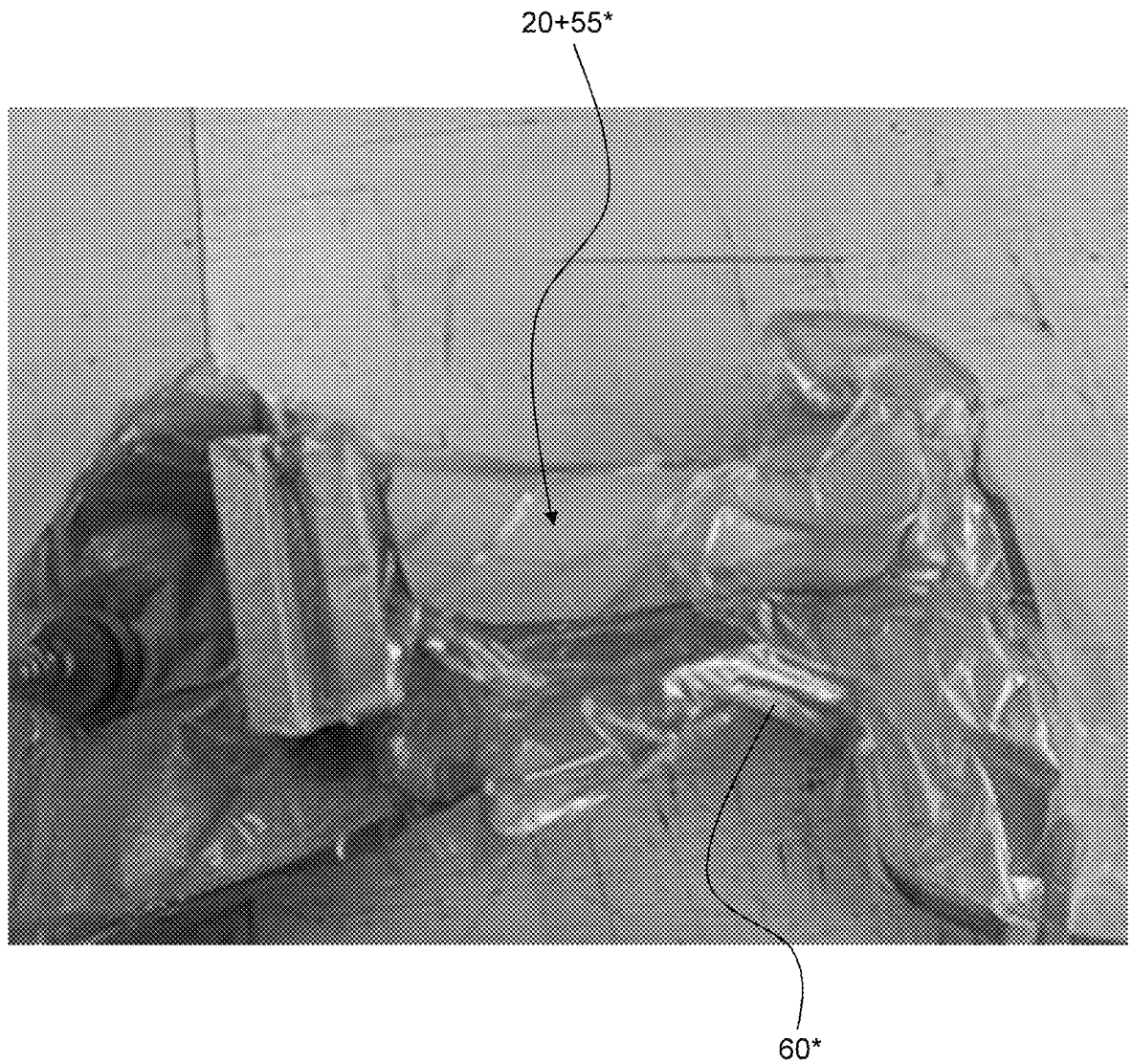
FIG. 6C is a photographic illustration of the vacuum bag of FIG. 6B after application of vacuum.

While FIG. 6B shows use of a standard vacuum bag 60, it is advantageous to use a vacuum bag having a custom shape conforming to the shape of the desired medical splint or brace, which prevents or reduces formation of wrinkles during application of vacuum to the vacuum bag.

Figure 7A:
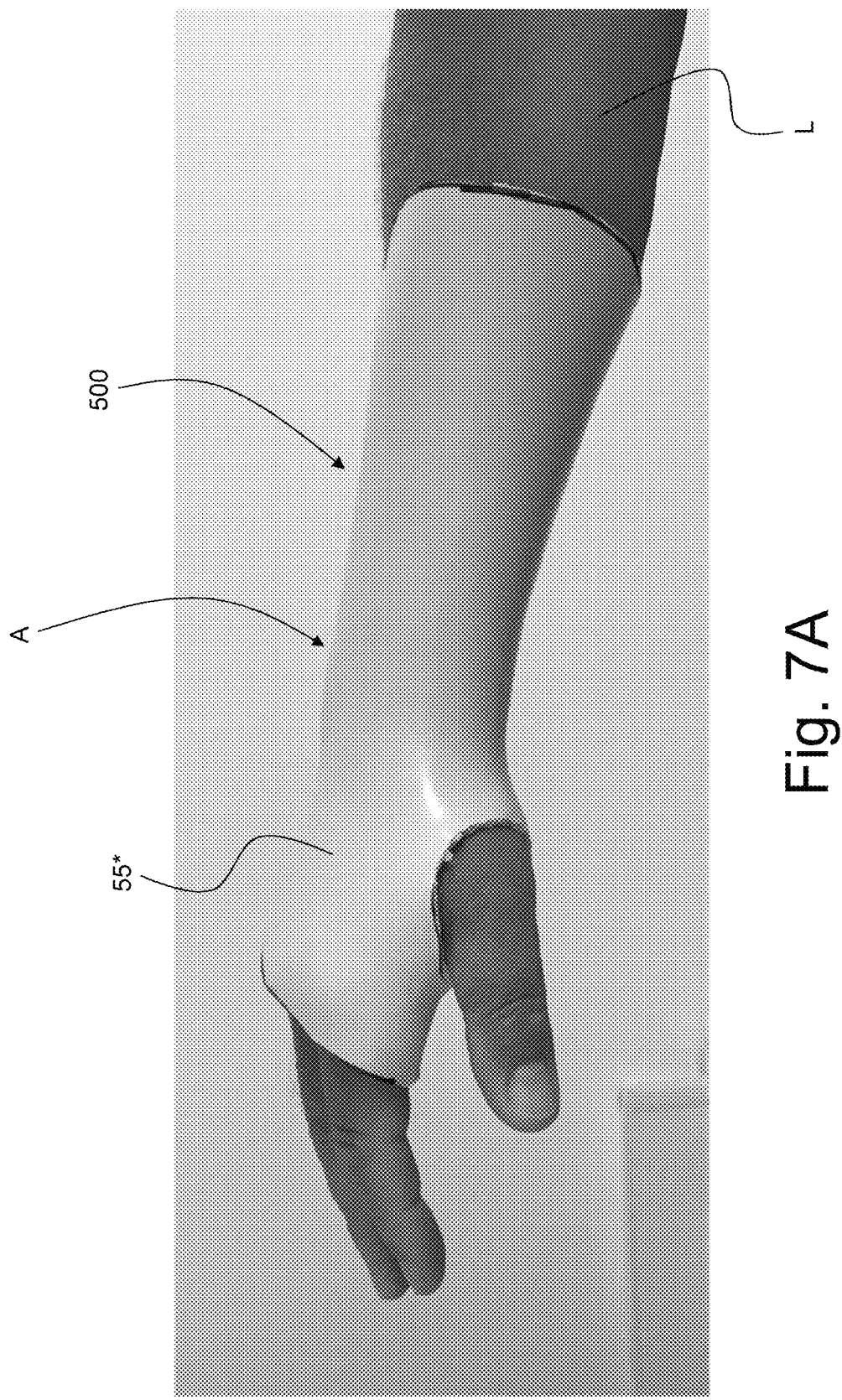
FIGS. 7A and 7B are photographic illustrations of a resulting splint or brace as produced in accordance with the invention.
Figure 7B:
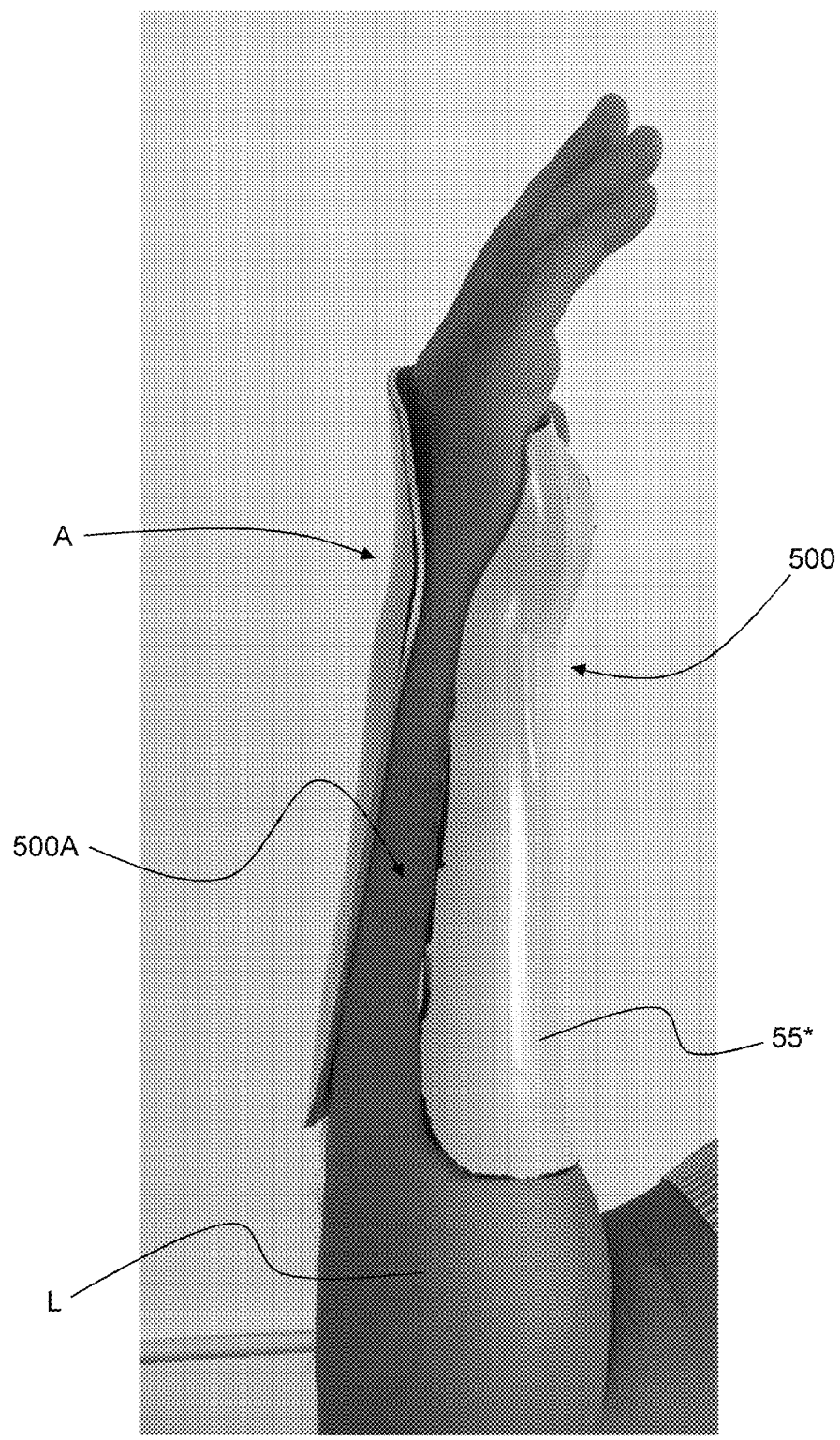

The resulting splint or brace 500 is shown in FIGS. 7A and 7B and can easily be finalized and adjusted onto the selected region A of the patient's limb L.

In accordance with a further embodiment of the invention, the production method may further comprise the step of forming one or more apertures or cut-outs in the plate of mouldable material. This can be performed either before or after moulding of the plate onto the three-dimensional mould. Preferably, such apertures and cut-outs are formed in the plate prior to moulding on the three-dimensional mould as the plate is still in a substantially planar configuration, which facilitates machining.

As this will be apparent from reading the above, the relevant three-dimensional shape of the splint or brace can be defined with great freedom allowing due consideration of the patient's actual lesions and the potential presence of wounds in the selected region to be immobilized. The splint or brace can furthermore be designed so as to improve comfort for the patient and allow swelling of the selected region being immobilized. In that respect, FIG. 7B for instance shows that the splint or brace 500 can be designed to exhibit a longitudinal slit 500A in the ulnar region of the forearm, which also facilitates placement and removal of the splint or brace 500 onto and, respectively, from the selected region A of the patient's body part L.

Thanks to the invention, the relevant splint or brace may be produced in a very short timeframe, especially within two hours. Furthermore, multiple splints or braces may be produced for a given patient, with good repeatability.

Various modifications and/or improvements may be made to the above-described embodiments without departing from the scope of the invention as defined by the annexed claims. In particular, while embodiments of the invention have been described for the purpose of immobilizing a patient's wrist, the invention is generally applicable to the immobilization of any selected region of a patient's body part.

Furthermore, while embodiments of the invention have been described in connection with the use of a plate of thermoformable material as mouldable material, the relevant plate could be made of any suitable mouldable material such as resin impregnated fabric or the like.

The splint or brace of the invention can be made of a single plate of mouldable material or several plates. In that respect, the invention is also meant to encompass splints or braces consisting of two or more individual components that are ultimately secured one to the other to form a relevant splint or brace. Any shape of splint or brace could in essence be contemplated in the context of the present invention. The invention can for instance be applied to the production of so-called bivalve splints or braces, as well as spiral splints or braces. The addition of clamping or tightening mechanisms as well as hinges could also be contemplated, as well as the addition of smart devices or sensors, for instance pressure sensors designed to measure or monitor the pressure exerted by the splint or brace onto the relevant portion of the patient's body part.

LIST OF REFERENCE NUMERALS AND SIGNS USED THEREIN

L patient's body part (e.g. human's limb/right forearm)
A selected region of patient's body part L to be immobilized (e.g. wrist)
100 three-dimensional scan of a portion of the patient's body part L, namely of the patient's right forearm, including the selected region A of the patient's limb L to be immobilized
10 three-dimensional digital model of the relevant portion of the patient's limb L as derived from the three-dimensional scan 100
20 three-dimensional mould of the relevant portion of the patient's limb L
20A base member of three-dimensional mould 20 designed to support three-dimensional mould 20 in a substantially vertical configuration
30 support material (e.g. tape material) applied on three-dimensional mould with a view to define and delimit a three-dimensional shape of the desired splint or brace
35 flattened support material 30 delimiting the three-dimensional shape of the desired splint or brace sheet of template material
40 two-dimensional template of the desired splint or brace
50 plate of mouldable material (e.g. Orfit™ material)
55 plate of mouldable material 50 roughly moulded onto three-dimensional mould 20
60 vacuum bag (prior to application of vacuum)
60* vacuum bag (after application of vacuum)
55* plate of mouldable material 50 as finally moulded onto three-dimensional mould 20
500 resulting splint or brace
500A longitudinal slit along the length of the splint or brace 500
200 pre-processed standardized block of material for production of three-dimensional mould 20 by milling
250 pre-processed standardized block of material for production of three-dimensional mould 20 by additive manufacturing

The invention claimed is:

1. A method of producing a custom medical splint or brace for immobilization of a selected region of a patient's body part, comprising the following steps:
producing a three-dimensional mold of a portion of the patient's body part comprising the selected region of the patient's body part onto which a desired medical splint or brace is to be placed;
after the producing the three-dimensional mold of the portion of the patient's body part, defining a three-dimensional shape of the desired medical splint or brace covering the selected region of the patient's body part onto which the desired medical splint or brace is to be placed;

generating a two-dimensional template of the desired medical splint or brace corresponding to the defined three-dimensional shape, wherein the two-dimensional template corresponds to unfolding in a two-dimensional plane of the three-dimensional shape of the desired medical splint or brace;

producing at least one plate of moldable material in accordance with the two-dimensional template of the desired medical splint or brace; and molding the plate of moldable material onto the three-dimensional mold to shape the desired medical splint or brace.

2. The method according to claim 1, wherein the plate of moldable material is made of a thermoformable material, which is heated to an activation temperature prior to molding thereof onto the three-dimensional mold.

3. The method according to claim 2, wherein the three-dimensional mold is made of a material having a melting point that exceeds the activation temperature of the thermoformable material.

4. The method according to claim 3, wherein the three-dimensional mold is made of polyurethane.

5. The method according to claim 1, wherein the three-dimensional mold is produced on the basis of a three-dimensional digital model of the portion of the patient's body part.

6. The method according to claim 5, wherein the three-dimensional digital model of the portion of the patient's body part is a three-dimensional digital model of a portion of a patient's limb, and wherein the three-dimensional digital model of the portion of the patient's limb is generated by three-dimensional imaging of the portion of the patient's limb onto which the splint or brace is to be placed or a mirrored image of a corresponding portion of the patient's contralateral limb.

7. The method according to claim 5, wherein the three-dimensional mold is produced at least partly by milling on a CNC milling machine.

8. The method according to claim 7, wherein the three-dimensional mold is produced from a standardized pre-processed block of material matching a given population of patients, wherein the standardized pre-processed block is subjected to milling.

9. The method according to claim 5, wherein the three-dimensional mold is produced at least partly by additive manufacturing.

10. The method according to claim 9, wherein the three-dimensional mold is produced from a standardized pre-processed block of material matching a given population of patients, wherein the standardized pre-processed block is subjected to additive manufacturing.

11. A method of producing a custom medical splint or brace for immobilization of a selected region of a patient's body part comprising the following steps:

producing a three-dimensional mould of a portion of the patient's body part comprising the selected region of the patient's body part onto which a desired medical splint or brace is to be placed;

defining a three-dimensional shape of the desired medical splint or brace covering the selected region of the patient's body part onto which the desired medical splint or brace is to be placed, wherein the three-dimensional shape of the desired medical splint or brace is defined by applying support material onto the three-dimensional mold covering the selected region where the desired medical splint or brace is to be placed and delimiting the three-dimensional shape of the desired medical splint or brace by means of the support material, generating a two-dimensional template of the desired medical splint or brace corresponding to the defined three-dimensional shape, wherein the two-dimensional template corresponds to unfolding in a two-dimensional plane of the three-dimensional shape of the desired medical splint or brace, wherein the two-dimensional template is generated by removing the support material with the three-dimensional shape delimited thereon from the three-dimensional mold and flattening the support material to cause unfolding of the three-dimensional shape in the two-dimensional plane, producing at least one plate of mouldable material in accordance with the two-dimensional template of the desired medical splint or brace; and moulding the plate of mouldable material onto the three-dimensional mould to shape the desired medical splint or brace.

12. A method of producing a custom medical splint or brace for immobilization of a selected region of a patient's body part, comprising the following steps:

producing a three-dimensional mould of a portion of the patient's body part comprising the selected region of the patient's body part onto which a desired medical splint or brace is to be placed;

defining a three-dimensional shape of the desired medical splint or brace covering the selected region of the patient's body part onto which the desired medical splint or brace is to be placed, wherein the three-dimensional shape of the desired medical splint or brace is defined in a digital environment by delimiting the three-dimensional shape of the desired medical splint or brace onto a three-dimensional digital model of the portion of the patient's body part corresponding to the three-dimensional mold, generating a two-dimensional template of the desired medical splint or brace corresponding to the defined three-dimensional shape, wherein the two-dimensional template corresponds to unfolding in a two-dimensional plane of the three-dimensional shape of the desired medical splint or brace, wherein the two-dimensional template is generated by digitally processing the three-dimensional shape to unfold the three-dimensional shape in the two-dimensional plane, producing at least one plate of mouldable material in accordance with the two-dimensional template of the desired medical splint or brace; and moulding the plate of mouldable material onto the three-dimensional mould to shape the desired medical splint or brace.

13. The method according to claim 1, wherein the three-dimensional mold is provided with a base member designed to support the three-dimensional mold in a substantially vertical configuration.

14. The method according to claim 1, wherein molding of the plate of moldable material onto the three-dimensional mold is carried out entirely by hand.

15. The method according to claim 1, wherein molding of the plate of moldable material onto the three-dimensional mold is carried out under vacuum.

16. The method according to claim 15, wherein the plate of moldable material is roughly molded onto the three-dimensional mold, wherein the three-dimensional mold is placed, together with the molded plate of moldable material, into a vacuum bag, and wherein vacuum is applied to the vacuum bag to cause final molding of the plate of moldable material onto the three-dimensional mold.

17. The method according to claim 16, wherein the vacuum bag has a custom shape conforming to the shape of the desired medical splint or brace to prevent or reduce formation of wrinkles during application of vacuum to the vacuum bag.

18. The method according to claim 1, further comprising the step of forming one or more apertures or cut-outs in the plate of moldable material.

19. The method according to claim 18, wherein the step of forming one or more apertures or cut-outs in the plate of moldable material is carried out prior to molding on the three-dimensional mold.

20. The method according to claim 1, wherein the medical splint or brace is produced by molding of a single plate of moldable material.

21. The method according to claim 1, wherein the medical splint or brace is produced by molding of a single plate of thermoformable material.

22. The method according to claim 1, wherein the medical splint or brace is configured to act as an external immobilization device placed around the selected region of the patient's body part.

23. The method according to claim 1, wherein the medical splint or brace is configured to act as an implantable immobilization device placed in the selected region of the patient's body part.

* * * * *